United States Patent [19]
Miller

[11] Patent Number: 5,640,974
[45] Date of Patent: Jun. 24, 1997

[54] KIT INCLUDING A CHIN SUPPORT MEMBER AND A NASAL PASSAGE DILATOR

[76] Inventor: Dale D. Miller, 4801 Indigo Dr., Wausau, Wis. 54401

[21] Appl. No.: 593,326

[22] Filed: Jan. 31, 1996

Related U.S. Application Data

[63] Continuation-in-part of Ser. No. 563,653, Nov. 28, 1995.

[51] Int. Cl.$^6$ .................................................. A61G 15/00
[52] U.S. Cl. ........................ 128/845; 128/848; 602/902; 606/204.45
[58] Field of Search .................................. 128/846, 848, 128/859–862, 62 A, 200.24, 207.18; 2/2; 602/902; 606/199, 204.45

[56] References Cited

U.S. PATENT DOCUMENTS

| | | | |
|---|---|---|---|
| 469,594 | 2/1892 | Perou | 128/848 |
| 746,869 | 12/1903 | Moulton . | |
| 774,446 | 11/1904 | Moulton . | |
| 1,354,652 | 10/1920 | Jefferies | 128/848 |
| 1,629,892 | 5/1927 | Storms | 128/848 |
| 1,674,336 | 6/1928 | King . | |
| 2,178,128 | 10/1939 | Waite | 128/136 |
| 4,711,237 | 12/1987 | Kaiser | 128/859 |
| 4,817,636 | 4/1989 | Woods | 128/848 |
| 5,476,091 | 12/1995 | Johnson | 128/200.24 |

OTHER PUBLICATIONS

Breathe Right Nasal Strips Promotional Material, Manufactured by CNS, Inc., 1994.

*Primary Examiner*—Michael A. Brown
*Attorney, Agent, or Firm*—Andrus, Sceales, Starke & Sawall

[57] ABSTRACT

A kit to promote effective breathing through nasal passages when a user is sleeping includes a chin support member and a nasal passage dilator. The chin support member is made of a flexible sheet or the like having an adhesive back that is designed to be applied to a user's face. The chin support member has a chin support portion that fits on a user's face underneath a user's mouth, and a first and second cheek attachment portion which adhere to the user's face above the user's mouth. The chin support member is configured so that the chin support portion supports the user's lower lip upward against the user's upper lip to keep the user's mouth naturally closed while the user is sleeping. However, the chin support member does not significantly cover the upper lip, and does not significantly restrict movement of the upper lip. A user is therefore able to cough or otherwise expel air or phlegm through the mouth while sleeping. When the chin support member is in place, a sleeping user instinctively and naturally breathes through his nose. The nasal passage dilator is preferably an external nasal passage dilator having an adhesive back that adheres across the user's nose and applies outward force to help open the user's nasal passages. In combination, the chin support member and the external nasal passage dilator effectively keep nasal passages clear and promote restful sleep, as well as reduce or eliminate irritating snoring noises. The kit can even provide relief to many people experiencing episodes of sleep apnea without the use of medication or expensive equipment.

7 Claims, 2 Drawing Sheets

KIT INCLUDING A CHIN SUPPORT MEMBER AND A NASAL PASSAGE DILATOR

This application is a continuation-in-part application of application Ser. No. 08/563,653, filed on Nov. 28, 1995.

BACKGROUND OF THE INVENTION

Many people wake up with varying degrees of congestion in their nasal passages. Such congestion can be quite uncomfortable, and can disturb the sleep of the person with congested nasal passages. Some people take medication or use elaborate medical apparatus to relieve nighttime congestion. It has been found that keeping the chin up and the mouth closed during sleep causes people to instinctively and naturally breath through their nose, thus keeping the nasal passages more clear of congestion and allowing more restful sleep.

Prior art anti-snoring mouthpieces are not believed to be widely used. Some of these devices require inserting an object into the nose or mouth, which can be uncomfortable. The device disclosed in U.S. Pat. No. 4,817,636 is a flexible sheet having an adhesive back that is used to tape a user's mouth closed while sleeping, thereby causing the user to breath through their nose. The device in U.S. Pat. No. 4,817,636 immobilizes both the lower and the upper lips as it covers the mouth. The device therefore prevents the user from naturally coughing or otherwise naturally expelling air, moisture or phlegm through the mouth while sleeping, or during brief periods of waking. The user of such a device risks the possibility (or at least the fear) of backblasting air or phlegm into their nasal passages or lungs if they cough while sleeping. Also, the device can be blasted off entirely.

It can therefore be appreciated that it would be desirable, at least for people suffering from nighttime nasal congestion, to provide a product that is convenient to use, and that is capable of keeping a user's mouth naturally closed while sleeping without running the risk of backblast.

It is known in the art to use nasal passage dilators to keep the nasal passages open and promote effective breathing through the nose. Such dilators have been used to reduce mouth breathing while sleeping, thus reducing congestion that can occur with mouth breathing while sleeping. An external nasal passage dilator such as shown in U.S. Pat. No. 5,476,091, by Bruce C. Johnson, entitled "Dilator for Anatomical Outer Wall Tissues Which is Adhesively Mounted" provides a convenient way to help keep a user's nasal passages open during sleep thus reducing nasal blockages that can lead to sleep disturbances, sleep irregularities, snoring, or a combination thereof. However, while the use of a nasal passage dilator may help to keep a user's nasal passages open, such dilators do not provide mechanical means to keep the user's mouth closed during sleep.

SUMMARY OF THE INVENTION

The invention is a kit including a chin support member and a nasal passage dilator that can help keep nasal passages clear and reduce snoring when a user uses the kit while sleeping. The chin support member is a flexible sheet having an adhesive back that is configured to accomplish a chin-up position and support a user's lower lip to keep the user's mouth naturally closed, and not sealed shut, while sleeping. The chin support member therefore promotes breathing through the nose while sleeping. The nasal passage dilator, preferably an external nasal passage dilator, helps keep the user's nasal passages open, thereby further promoting effective breathing through the nose while sleeping.

The chin support member is preferably made of a flexible sheet having a hypo-allergenic adhesive back that adheres to a user's face. The chin support member is configured to support the user's lower lip upward and keep the user's mouth naturally closed when sleeping. The member does not significantly restrict movement of the user's upper lip so the user can expel air or phlegm easily through the mouth while sleeping. A conscious command is required by the user to open the user's mouth to intake air, but not to expel fluid or air. Limited voice use is also possible while wearing the product because the upper lip can move while the product is in place.

The nasal passage dilator in the kit is preferably an external nasal passage dilator such as described in above-referenced U.S. Pat. No. 5,476,091, entitled "Dilator for Anatomical Outer Wall Tissues Which is Adhesively Mounted" by Bruce C. Johnson, which is incorporated by reference herein. Using the nasal passage dilator in combination with the chin support member provides a convenient way to promote effective breathing through the nose while the user's mouth is kept naturally closed when sleeping.

The preferred chin support member consists of a chin support portion that is intended to be attached to the user's face below the user's lower lip, and a first and second cheek attachment portion. The first cheek attachment portion extends generally upward from one end of the chin support portion, and the second cheek attachment portion extends upward from the other end of the chin support portion. The chin support member is sized so that the first and second cheek attachment portions adhere to the user's face above the user's mouth when the chin support portion is placed underneath the user's mouth. The upper edge of the chin support portion supports the user's lower lip upward against the user's upper lip to keep the user's mouth naturally closed during sleep. The upper edge of the chin support portion preferably spans horizontally between the first and second cheek attachment portions.

It is preferred that the first and second cheek attachment portions cover only the remote ends of the user's lips when the chin support member is attached to the user's face. As long as the chin support member does not significantly restrict movement of the user's upper lip, a cough will not backblast into the nose and lungs of the user or will not blast the chin support member off the face of the user.

The chin support member can be made from hypo-allergenic cloth tape such as sold by Johnson & Johnson Consumer Products, Inc., New Brunswick, N.J. under the tradename Dermicel®. Alternatively, the chin support member can be made of a suitable tear-resistant polymer or paper products. Some manufacturers may prefer to pad or layer the chin support member.

The components of the kit are intended to be disposable. Individual units of the chin support member and the external nasal passage dilator can be packaged together.

The primary object of the invention is to provide a convenient to use kit that will keep nasal passages clear and promote effective breathing through the nose while sleeping. It has been discovered, however, that the invention can also reduce the loudness of snoring, and in some cases can even eliminate snoring all together over a period of extended use. The invention can also provide relief to many people experiencing episodes of sleep apnea without the use of medication or expensive equipment.

Other features, objects and advantages of the invention should be apparent to those skilled in the art upon reviewing the drawings and the following description thereof.

BRIEF DESCRIPTION OF THE DRAWINGS

Parent Application

Present Application

Figure 6:
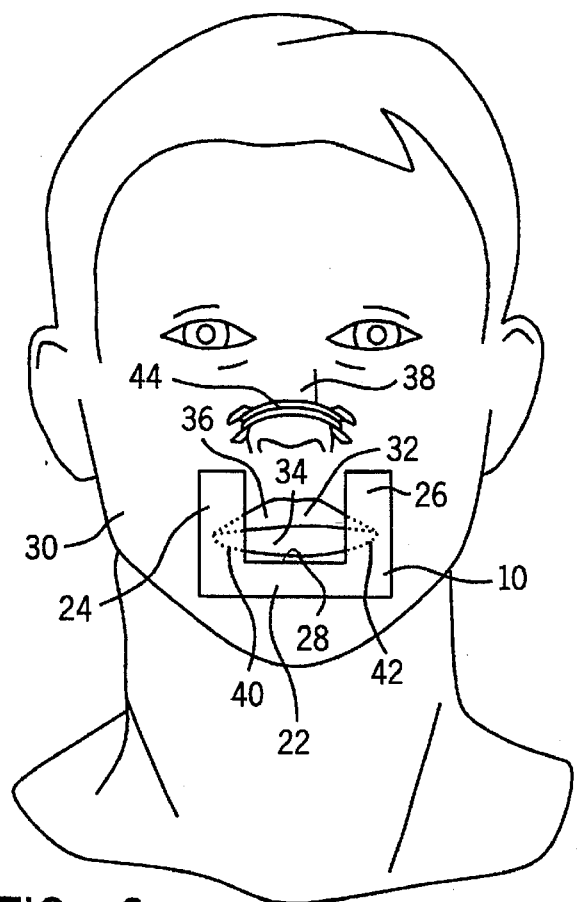

FIG. 6 is a schematic view illustrating the use of a kit in accordance with the invention of the present application.

DETAILED DESCRIPTION OF THE PREFERRED EMBODIMENTS

Parent Application

Figure 1:
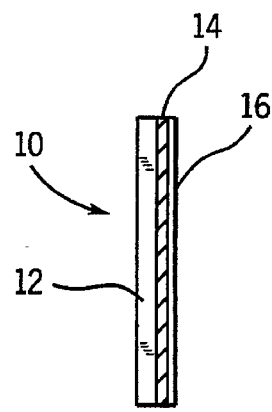
FIG. 1 is a side elevational view of a chin support member in accordance with the invention of the parent application.
Figure 2:
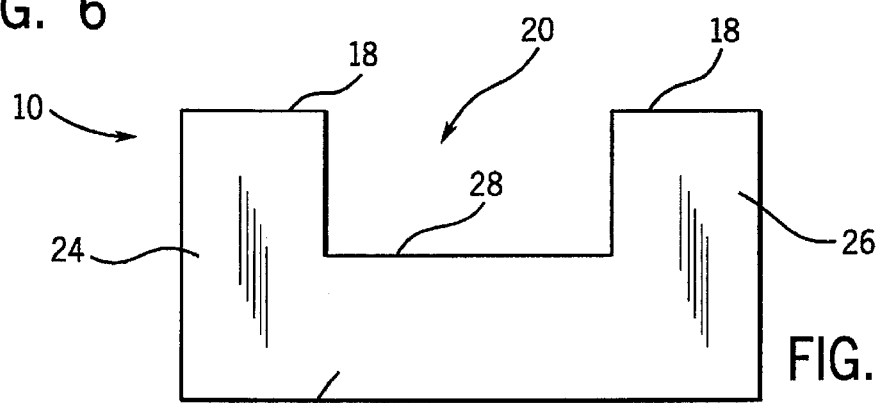
FIG. 2 is a front elevational view of a first embodiment of the invention described in the parent application.
Figure 4:
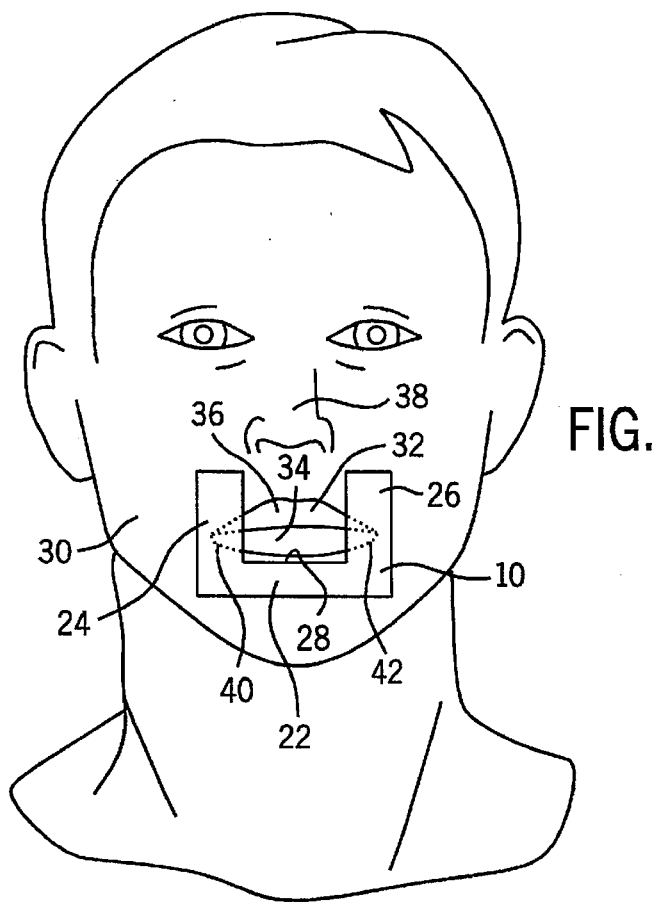
FIG. 4 is a schematic view illustrating the use of the embodiment of the invention described in the parent application and shown in FIG. 2.

In FIGS. 1, 2 and 4 which depict a first embodiment of the invention described in the parent application, the illustrated chin support member 10 is made of a flexible sheet 12 having an adhesive backing 14, and optionally a back sheet 16 that covers the hypo-allergenic adhesive backing 14. Hypo-allergenic adhesive is applied to the entire back surface of the chin support member 10. Adhesives on commonly used medical tape or bandages may be used. The chin support member 10 can be made of hypo-allergenic cloth tape such as is sold by Johnson & Johnson Consumer Products, Inc., New Brunswick, N.J. under the name Dermicel®. The chin support member 10 can be made from other types of tape having a hypo-allergenic adhesive backing including paper or polymer tear-resistant tapes. It may be desirable to construct the product from a combination of sheets of paper, cloth, or the like to make a padded or layered chin support member 10.

Figure 3:
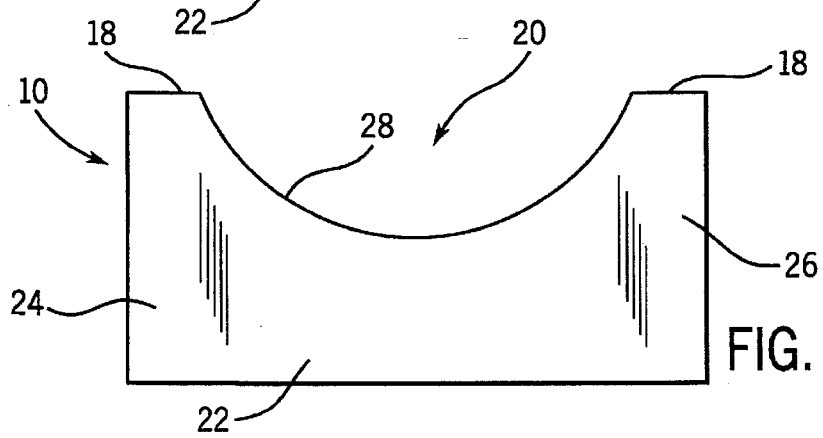
FIG. 3 is a front elevational view of a second embodiment of the invention described in the parent application.

In the embodiment of the invention shown in FIGS. 2, 3 and 4, the chin support member 10 consists of a rectangular sheet. The upper edge 18 of the rectangular sheet has an indentation depicted by arrow 20. Due to the indentation 20, the chin support member 10 can be thought of as having three distinct portions: a chin support portion 22, a first cheek attachment portion 24, and a second cheek attachment portion 26.

Referring in particular to FIG. 2, the preferred chin support member 10 consists of a rectangle having about a 4.5 inch base and about a 2.5 inch height along the outer edges. The indentation 20 creates a center open portion at the top of the member 10 having about a 1–1½ width and about a 1 inch depth from the top edge 18 of the member 10. The specific dimensions of the units can be varied to accommodate individual mouth and facial dimensions.

The bottom of the indentation 20 defines an upper edge 28 of the chin support portion 22. It is preferred that the upper edge 28 of the chin support portion 22 span horizontally between the first and second cheek attachment portions 24 and 26. In FIG. 2, the chin support portion 22 is generally rectangular and perpendicular to the first and second cheek attachment portions 24 and 26. In FIG. 3, the chin support portion 22 is likewise substantially perpendicular to the first and second cheek attachment portions 24 and 26. However, in FIG. 3, the indentation 20 is not rectangular, and thus the cheek chin support portion 22 is not rectangular. Even in the embodiment shown in FIG. 3, it is preferred that the upper edge 28 of the chin support portion 22 be substantially horizontal. The substantially horizontal upper edge 28 promotes effective support of the user's lower lip to accomplish a natural "chin-up" position during sleep.

Referring now to FIG. 4, the chin support member 10 is sized so that the chin support portion 22 fits on a user's face 30 underneath the user's mouth 32 when the member 10 is in place on to the user's face 30. The first cheek attachment portion 24, and the second cheek attachment portion 26 adhere to the user's face 30 above the user's mouth 32. The upper edge 28 of the chin support portion 22 supports the user's lower lip 34 upward against the user's upper lip 36 so that the user instinctively and naturally breathes through his nose 38 when sleeping. As shown in FIG. 4, the first cheek attachment portion 24 covers a first remote end 40 of the user's lips when the chin support member 10 is in place on the user's face 30. The second cheek attachment portion 26 covers a second remote end 42 of the user's lips when the chin support member 10 is in place on the user's face 30. Note that the chin support member 10 does not significantly restrict movement of the user's upper lip 36. The chin support member 10 therefore allows the user to expel air, moisture or phlegm while sleeping without running the risk of backblast. The chin support member also allows limited voice use when the member 10 is in place.

While it is intended that upper edge 28 of the chin support portion 22 be located slightly below the user's lower lip 34 when the chin support member 10 is in place, some people may prefer to place the chin support member 10 so that the upper edge 28 resides on the lower lip 34.

Figure 5:
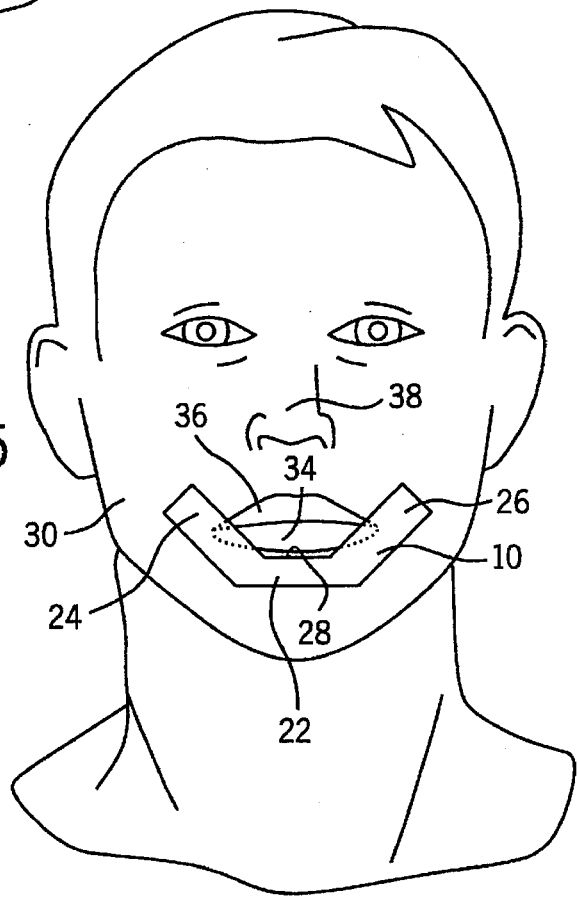
FIG. 5 is a schematic drawing illustrating the use of yet another embodiment of the invention described in the parent application.

Referring now to FIG. 5, another embodiment of the chin support member 10 is illustrated in place on a user's face 30. In this embodiment, the first and second cheek attachment portions 24 and 26 extend outward at an angle as they extend upward, thereby defining a flat-bottom, V-type configuration for the chin support member 10. The flat-bottom, V-type configuration shown in FIG. 5 is illustrated to clearly point out that the invention is not limited to the specific dimensions and/or geometries depicted in the drawings.

Present Application

FIG. 6 shows the use of a kit including a chin support member 10 and an external nasal passage dilator 44 in accordance with the invention of the present application. The chin support member 10 shown in FIG. 6 is the same configuration as the chin support member 10 shown in FIG. 4, and operates in the same manner as the chin support member 10 shown in FIG. 4.

The external nasal passage dilator 44 is preferably similar to the nasal passage dilator described in above-incorporated U.S. Pat. No. 5,476,091, and those skilled in the art can reference U.S. Pat. No. 5,476,091 for an explanation of the preferred way to make and use dilator 44.

In brief, dilator 44 is an adhesive strip having one or more trusses that provide small outward forces on the surface of the user's nose (e.g., 20–30 grams). The small outward forces help keep the nasal passages open when the user is breathing through the nose, even if there are obstructions in the nasal passages. The operation of the external nasal passage dilator can best be understood by referencing FIGS. 4–6 in the above-incorporated U.S. Pat. No. 5,476,091.

When using the kit, the chin support member 10 supports the user's lower lip to keep the user's mouth naturally closed while sleeping, thus promoting breathing through the nose. The external nasal passage dilator 44 helps keep the user's nasal passages open while sleeping, thereby further promoting effective nose breathing while sleeping. The kit including the combination of the chin support member 10 and the external nasal passage dilator 44 can therefore be especially effective in promoting efficient nighttime nose breathing, thereby reducing nighttime congestion and snoring. The kit can provide relief to many people experiencing episodes of sleep apnea without the use of medication or expensive equipment.

While the drawings show several embodiments of the invention, other modifications, alternatives or equivalents to the invention may be apparent to those skilled in the art. Such modifications, alternatives and equivalents should be considered to be within the scope of the following claims.

I claim:

1. A kit comprising:

a chin support member made of a flexible sheet having an adhesive back, the chin support member being comprised of a chin support portion having a first end and a second end, a first cheek attachment portion extending generally upward from the first end of the chin support portion, and a second cheek attachment portion extending generally upward form the second end of the chin support portion, wherein the chin support member is sized so that the chin support portion fits on a user's face underneath the user's mouth when the chin support member is adhered to the user's face, the first and second cheek attachment portions adhere to the user's face at locations higher than the user's mouth, and a upper edge of the chin support portion supports a user's lower lip to help keep the user's mouth naturally closed when the user is sleeping, and an area above the upper edge of the chin support portion and between the first cheek attachment portion and the second cheek attachment portion is completely open so that the chin support member does not substantially cover the user's mouth; and the kit further comprises a nasal passage dilator.

2. A kit as recited in claim 1 wherein the nasal passage dilator is an external nasal passage dilator having an adhesive back that is used to apply the dilator across the nose of the user.

3. A kit as recited in claim 1 wherein the upper edge of the chin support portion of the chin support member spans horizontally between the first and second cheek attachment portions.

4. A kit as recited in claim 1 wherein the adhesive back on the chin support member is hypo-allergenic.

5. A kit as recited in claim 1 wherein the chin support member includes a backing sheet that covers the adhesive back.

6. A kit as recited in claim 1 wherein the first cheek attachment portion of the chin support member covers a first remote end of the user's lips when the chin support member is attached to the user's face and the second cheek attachment portion of the chin support member covers a second remote end of the user's lips when the chin support member is attached to the user's face.

7. A kit as recited in claim 1 wherein the chin support member consists of a rectangular sheet or the like having two side edges, a lower edge and an upper edge, the upper edge having an indentation therein, thereby defining the chin support portion and the first and second cheek attachment portions in the chin support member.

* * * * *